(12) United States Patent
Yoneoka et al.

(10) Patent No.: US 7,097,725 B2
(45) Date of Patent: Aug. 29, 2006

(54) PLACEMENT DEVICE

(75) Inventors: Kikuo Yoneoka, Osaka (JP); Xu Joy, Osaka (JP); Katsutoshi Kishimoto, Osaka (JP)

(73) Assignee: Zuiko Corporation, Osaka (JP)

( * ) Notice: Subject to any disclaimer, the term of this patent is extended or adjusted under 35 U.S.C. 154(b) by 416 days.

(21) Appl. No.: 10/684,790

(22) Filed: Oct. 14, 2003

(65) Prior Publication Data

US 2004/0123954 A1 Jul. 1, 2004

(30) Foreign Application Priority Data

Oct. 16, 2002 (JP) .............................. 2002-301647

(51) Int. Cl.
*A61F 13/15* (2006.01)
*B32B 37/00* (2006.01)
(52) U.S. Cl. ...................... 156/161; 156/163; 156/164; 156/229; 156/494; 156/495; 156/496

(58) Field of Classification Search ................ 156/161, 156/163, 229, 164, 494, 495, 496
See application file for complete search history.

(56) References Cited

U.S. PATENT DOCUMENTS

| | | | | |
|---|---|---|---|---|
| 5,040,783 | A | * | 8/1991 | Ruehl ......................... 271/300 |
| 5,147,487 | A | * | 9/1992 | Nomura et al. ............. 156/164 |
| 5,389,173 | A | * | 2/1995 | Merkatoris et al. ......... 156/164 |
| 5,525,175 | A | * | 6/1996 | Blenke et al. .............. 156/161 |
| 6,895,649 | B1 | * | 5/2005 | Kojo et al. .............. 29/407.01 |
| 2003/0010423 | A1 | * | 1/2003 | Nakakado et al. .......... 156/164 |

* cited by examiner

*Primary Examiner*—Jeff H. Aftergut
(74) *Attorney, Agent, or Firm*—Renner, Otto, Boisselle and Sklar, LLP (57) ABSTRACT

A placement device, comprising: a guide section for guiding an elastic member; a first nip roll and a second nip roll for pressing together the elastic member and a web; a transfer section capable of transferring the guide section across the web; and an indicating section for indicating a position, wherein when the guide section comes close to the position while moving in a first direction, the transfer section can stop transferring the guide section in response to a signal from the indicating section.

12 Claims, 10 Drawing Sheets

PLACEMENT DEVICE

BACKGROUND OF THE INVENTION

1. Field of the Invention

The present invention relates to a placement device.

2. Description of the Related Art

In a disposable worn article such as a paper diaper, an elastic member is placed at a predetermined position for forming gathers (e.g., Japanese Laid-Open Patent Publication No. 9-70412). A gather control device described in this publication includes a pair of nip rolls for sandwiching an elastic member between two webs, and an aperture section for guiding the elastic member between the webs.

The device places the elastic member in a predetermined pattern on the web by moving the aperture section. The line along which the elastic member is placed varies for different sizes and designs of articles. If, for example, the position of the elastic member placed on the web along leg portions is shifted from the position of leg holes made in the web, a good product cannot be produced. Therefore, it is important to accurately form the line at a predetermined position.

However, the publication mentioned above fails to disclose a method for controlling the gather control device and other devices in phase with one another.

SUMMARY OF THE INVENTION

It is therefore an object of the present invention to provide a technique for achieving the phase match.

In order to achieve the object, the present invention provides a placement device, including: a guide section for guiding an elastic member; a first nip roll and a second nip roll for pressing together the elastic member and a web; a transfer section capable of transferring the guide section across the web; and an indicating section for indicating a position, wherein when the guide section comes close to the position while moving in a first direction, the transfer section stops transferring the guide section in response to a signal from the indicating section.

For example, in a case where the indicating section is a sensor which includes a photoelectric switch, or the like, the light-receiving portion of the sensor of the photoelectric switch has a predetermined width, a direction dependence hysteresis, insensitivity of sensing area, or the like, and a member is detected when the light-receiving portion is shaded. Therefore, the relative position of the photoelectric switch and the detected transfer section or guide section has an error corresponding to the width of the light-receiving portion, a direction dependence hysteresis, insensitivity of sensing area, or the like, depending on the direction in which the transfer section or the guide section approaches the sensor. This error translates into an error in the position of the transfer section or the guide section, thus resulting in an error in the line along which the elastic member is placed.

In contrast, with the present device, the position of the transfer section or the guide section is determined based on a signal from the sensor only when the transfer section or the guide section is moving in the first direction (a predetermined direction). Therefore, it is possible to accurately detect the position of the transfer section or the guide section, irrespective of the width of the sensing portion, a direction dependence hysteresis, insensitivity of sensing area, or the like. After placing the guide section at the position by using such a placement device, a cutter drum having a blade thereon is rotated, and the transfer section starts transferring the guide section when the blade comes to a predetermined position, whereby it is possible to easily control the placement device and the cutter drum in phase with each other.

In a placement device of the present invention, the transfer section includes a motor capable of rotating in a first rotation direction and a second rotation direction opposite to the first rotation direction, whereby a moving direction of the guide section can be changed by changing a rotation direction of the motor; the indicating section is a sensor for detecting the guide section or the transfer section, and is capable of indicating that the guide section is located at the position; and if the sensor detects the guide section or the transfer section when the rotation direction of the motor is the first direction, a controller stops the rotation of the motor.

The motor may be a servomotor that rotates according to predetermined control data. The control data for the servomotor may be determined based on a control pattern such as a predetermined velocity curve. The control pattern may be prestored in a storage device for each size and type of a product to be produced.

Since the guide section is provided adjacent to the nip rolls, it may be difficult to maintain when, for example, an adhesive applied on a web attaches to a roll or when a web or an elastic member is broken. In contrast, if at least one of the pair of nip rolls is movable away from the other nip roll, the rolls can be spaced apart from each other, thereby improving the maintainability. Moreover, if the placement device further includes a stand on which the transfer section is placed, and the stand is movable so that the distance between the nip point between the pair of nip rolls and the guide section can be changed, the guide section can be moved away from the nip point when maintaining the device, thereby further improving the maintainability. Furthermore, if the stand can be pulled out from under the nip rolls along the axial direction of the nip rolls, the guide section or the transfer section can be moved to a more spacious place for easy maintenance, thus further improving the maintainability.

An adhesive for fixing together the web and the elastic member may be applied continuously or intermittently on the web. In a case where a single web is used, it is preferred that the nip roll that is to be in contact with the adhesive is covered with a material having a good peelability in order to prevent the adhesive from attaching to the nip roll.

Moreover, the elastic member may be sandwiched between the web and another web. By sandwiching the elastic member between two webs, it is possible to reliably fix or restrict the position of the elastic member. An adhesive for fixing the elastic member is applied continuously or intermittently on at least one of the webs.

Moreover, instead of bonding the elastic member directly on the web, the two webs may alternatively be bonded together so that the position of the elastic member is restricted by the bonded portions. In other words, the position of the elastic member is restricted by the two webs and an adhesive. For example, an adhesive is applied continuously or intermittently so as to surround the elastic member when the elastic member is placed on the web.

Moreover, the elastic member may include a heat-sealable member, and the elastic member and the web may be heat-sealed together by the first and second nip rolls. In this way, an adhesive is no longer needed, whereby it is possible to reduce the production cost.

Moreover, the first nip roll may include a plurality of protrusions while the second nip roll functions as an anvil so that the protrusions melt portions of the web and another web to bond the webs to each other at a plurality of bonding points, whereby the position of the elastic member is restricted by the plurality of bonding points. This also eliminates the need for an adhesive, allowing for a reduction in the production cost.

DESCRIPTION OF THE PREFERRED EMBODIMENTS

A preferred embodiment of the present invention will now be described with reference to the drawings. FIG. 1 to FIG. 8 illustrate one embodiment of the present invention.

Figure 1:
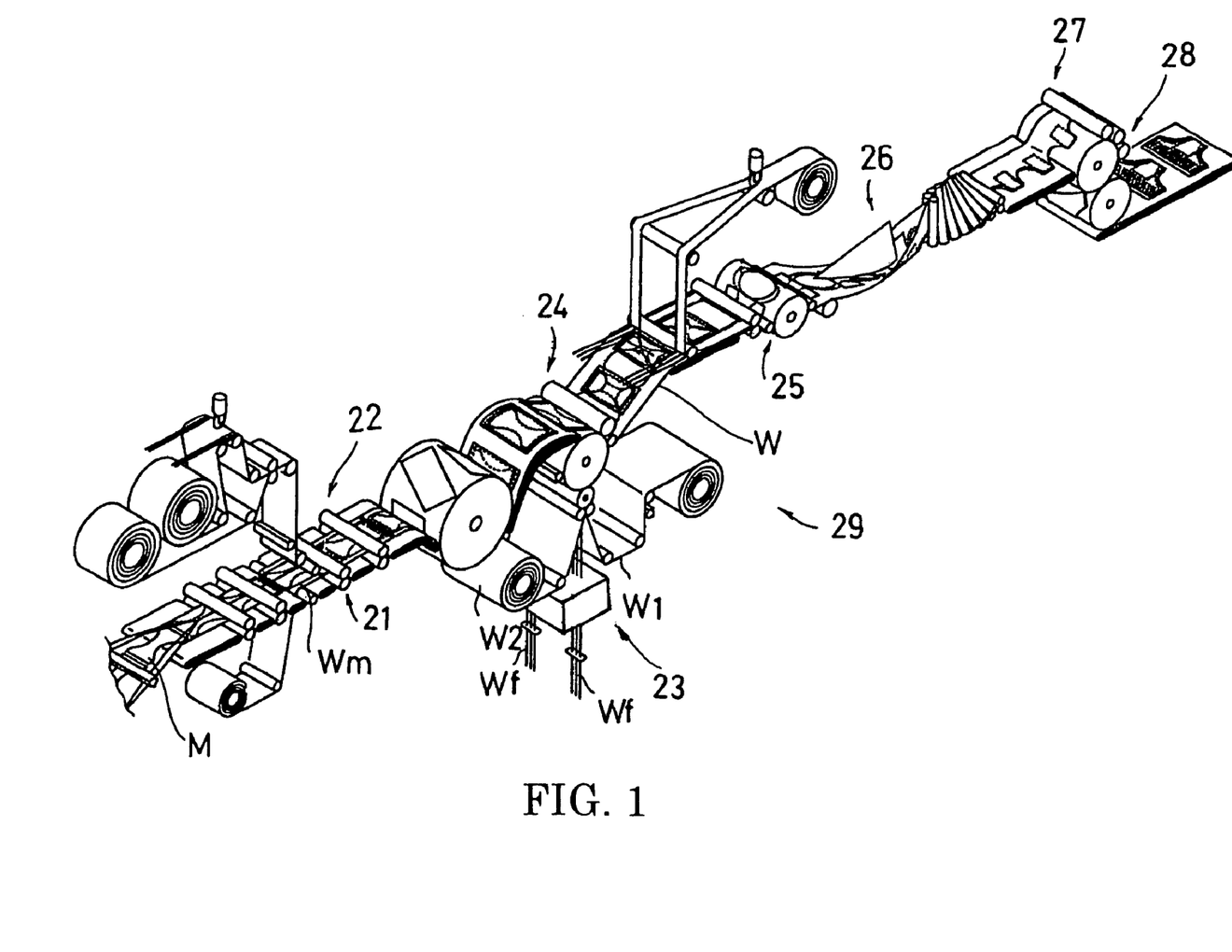
FIG. 1 is a perspective view illustrating an apparatus for producing an article according to an embodiment of the present invention.

FIG. 1 illustrates a production apparatus 29 for producing an article. The production apparatus 29 is capable of producing a pants-type diaper, which is a type of worn article, by placing an elastic member Wf in a predetermined pattern between webs W1 and W2 to form a combined web W, and placing a combined member Wm having a liquid-absorbing mat M on the combined web W.

The production apparatus 29 includes a first seal unit 21 for receiving the mat M, which has been cut off by a first cutter unit, covering the cut-off mat M with a web, and sealing an end of the combined member Wm, a second cutter unit 22 for cutting off the combined member Wm along the sealed portion or between the sealed portions, and a guide unit (device for placing an elastic member) 23 for guiding and placing the elastic member Wf between the webs W1 and W2. The sealing may be done by adhesive application or heat sealing.

The production apparatus 29 further includes an assembly unit 24 for placing the combined member Wm on the combined web W, into which the elastic member Wf has been placed, a trim cutter unit 25 for making a leg hole, etc., in the combined web W, a folding unit 26 for folding in two the combined web W with the leg hole, etc., made therein, a second seal unit 27 for sealing the boundary between semi-finished articles, and a third cutter unit 28 for cutting off the combined web W along the sealed portion or between the sealed portions into individual articles.

Figure 2:
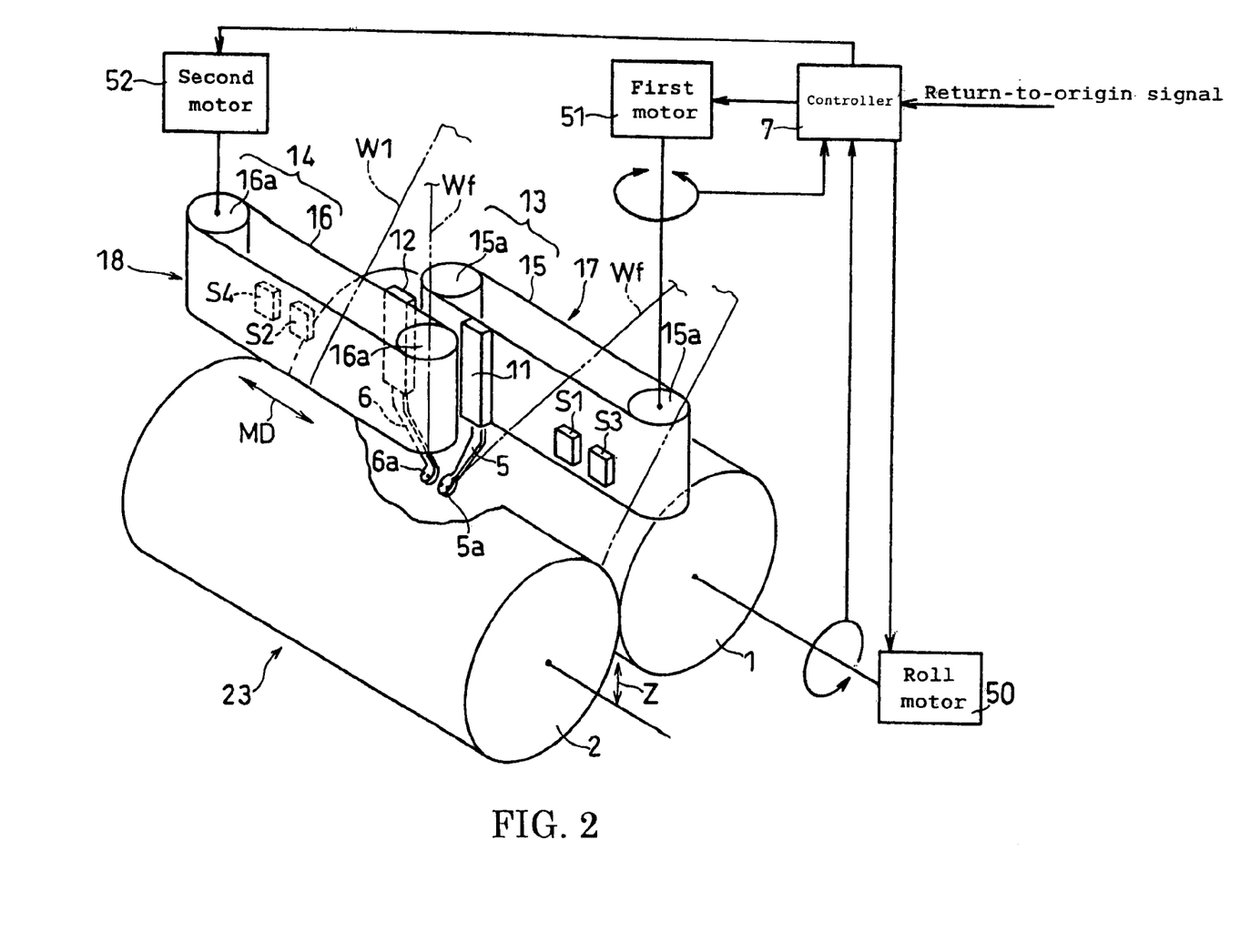
FIG. 2 is a perspective view illustrating a device for placing an elastic member, as viewed from below.
Figure 3:
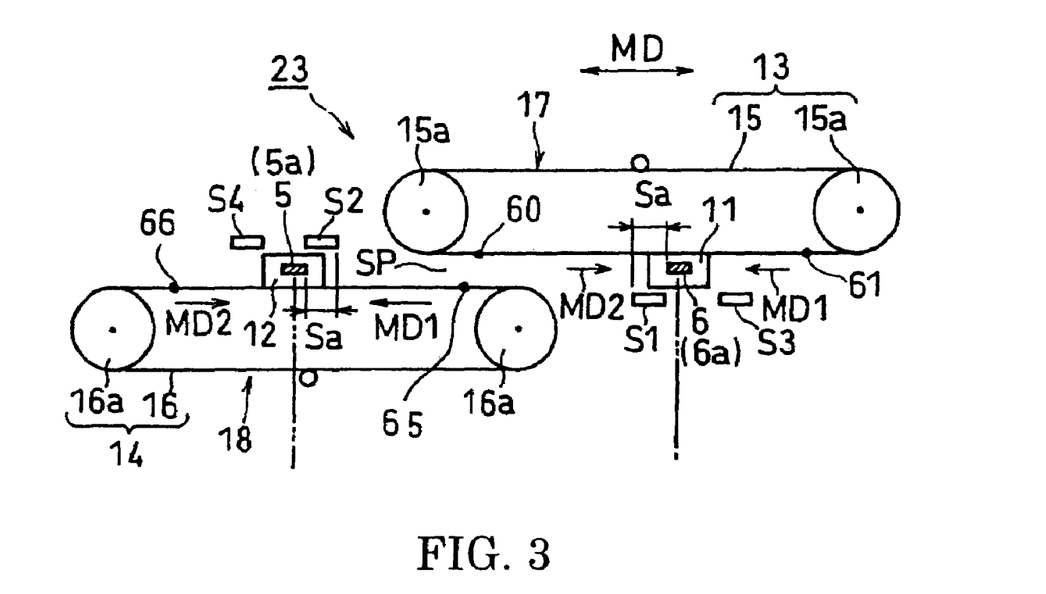
FIG. 3 is a schematic plan view illustrating the placement device.
Figure 4:
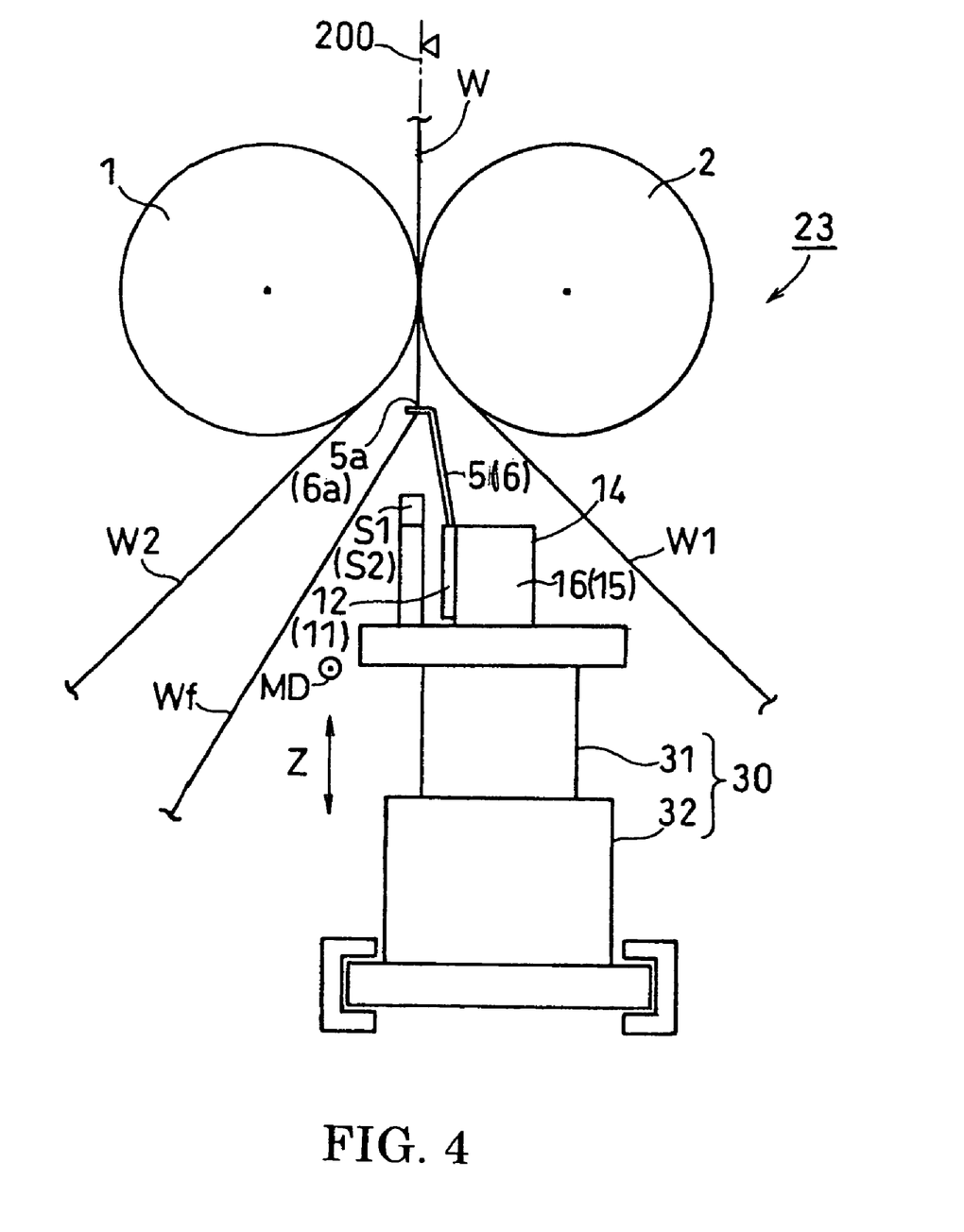
FIG. 4 is a schematic side view illustrating the placement device.

FIG. 2 is a partially-cutaway perspective view illustrating the guide unit 23 as viewed from below, FIG. 3 is a plan view of the unit, and FIG. 4 is a schematic side view of the unit.

The guide unit 23 includes nip rolls 1 and 2, a first moving member 17, and a second moving member 18.

The nip rolls 1 and 2 nip the webs W1 and W2 therebetween, along with the elastic member Wf between the webs W1 and W2. In the guide unit 23 as illustrated in FIG. 2, the nip rolls 1 and 2 are driven by a roll motor 50. The roll motor 50 may be a servomotor, for example. The roll motor 50 is controlled by a controller 7 to be described later. Alternatively, the driving power for the nip rolls 1 and 2 may be supplied from the production apparatus 29, instead of from the roll motor 50.

The guide unit 23 includes a first moving member 17 and a second moving member 18. The first moving member 17 includes a first arm (movement) 5 for guiding at least one elastic member Wf near the position where the nip rolls 1 and 2 meet each other (i.e., where they come in contact with, or closest to, each other), and a first transfer section 13 for transferring the first arm 5. The second moving member 18 includes a second arm (movement) 6 for guiding at least one elastic member Wf near the position where the nip rolls 1 and 2 meet each other, and a second transfer section 14 for transferring the second arm 6. The first transfer section 13 moves the first arm 5 across the first web W1. Similarly, the second transfer section 14 moves the second arm 6 across the second web W2.

FIG. 3 illustrates the first and second transfer sections 13 and 14, etc., of FIG. 2 from a direction opposite the nip rolls 1 and 2. The first transfer section 13 includes a pair of pulleys 15a and a belt 15 wound around the pulleys 15a, and the second transfer section 14 includes a pair of pulleys 16a and a belt 16 wound around the pulleys 16a. The first transfer section 13 is driven by a first motor 51. The second transfer section 14 is driven by a second motor 52 similar to the first motor 51. The first and second motors 51 and 52 may each be a servomotor, in which case the rotation of the motor, etc., can easily be controlled. The motors 51 and 52 are controlled based on a motor control pattern supplied from the controller 7, as will be described later.

Moreover, the first and second motors 51 and 52 connected to the pulleys 15a and 16a, respectively, may be placed away from each other near the opposite ends of the nip rolls 1 and 2, or may be placed closer to the middle of the nip rolls 1 and 2 in the width direction MD. Moreover, each pair of pulleys 15a (or 16a) may be driven by a pair of motors. In such a case, the belt may be rotated in the first direction by one of the pair of motors while the belt is rotated in the second direction, opposite from the first direction, by the other motor, thereby increasing the precision of the rotational position of the belt.

A first bracket 11 and a second bracket 12 are attached to the belts 15 and 16, respectively, and the arms 5 and 6 are fixed to the brackets 11 and 12, respectively. For example, the transfer sections 13 and 14 are placed facing each other, so that the first and second brackets 11 and 12 are moved in the space SP (FIG. 3) between the pair of transfer sections 13 and 14. As the belts 15 and 16 are moved, the brackets 11 and 12 are reciprocated across the web W1 (W2) in the width direction MD.

Note that the arrangement of the belts 15 and 16 is not limited to that shown in FIG. 3. The belts 15 and 16 may be arranged so that a level of the pulleys 15a is different from a level of the pulleys 16a. For example, the rotational axis of one pulley 16a of the belt 16 passes inside the loop of the belt 15 and the rotational axis of one pulley 15a of the belt 15 passes inside the loop of the belt 16. Then, a part of the belt 15 overlaps a part of the belt 16 in the rotational axis direction of the pulley 15a or the pulley 16a. In such a case, the brackets 11 and 12 may be arranged in the same side of the belts 15 and 16.

The first arm 5 includes at least one first guide section 5a for guiding the elastic member Wf near the position where the nip rolls 1 and 2 meet each other, and the second arm 6 includes at least one second guide section 6a similar to the first guide section 5a. The guide sections 5a and 6a may be placed generally along a virtual plane 200 shown in FIG. 4 (the plane at which the nip rolls 1 and 2 meet each other). Herein, "placed generally along" means that the guide sections 5a and 6a need not be placed completely along the plane 200. Depending on the shape of the guide sections 5a and 6a, they may cross the plane 200.

Note that the elastic member Wf may be supplied to the guide sections 5a and 6a while passing through the inside of the loops of the belts 15 and 16, respectively.

An adhesive is applied on at least one of the webs W1 and W2. The application may be continuous or intermittent. In a case where a hot melt is used as an adhesive, the hot melt may be applied by using any of beads, a coater, a spiral, a curtain, a spray, a transfer roll, etc. Types of hot melt that can be used include a synthetic rubber-based hot melt, an olefin-based hot melt, etc. Moreover, an adhesive as described above may be applied on the elastic member.

Figure 5A:
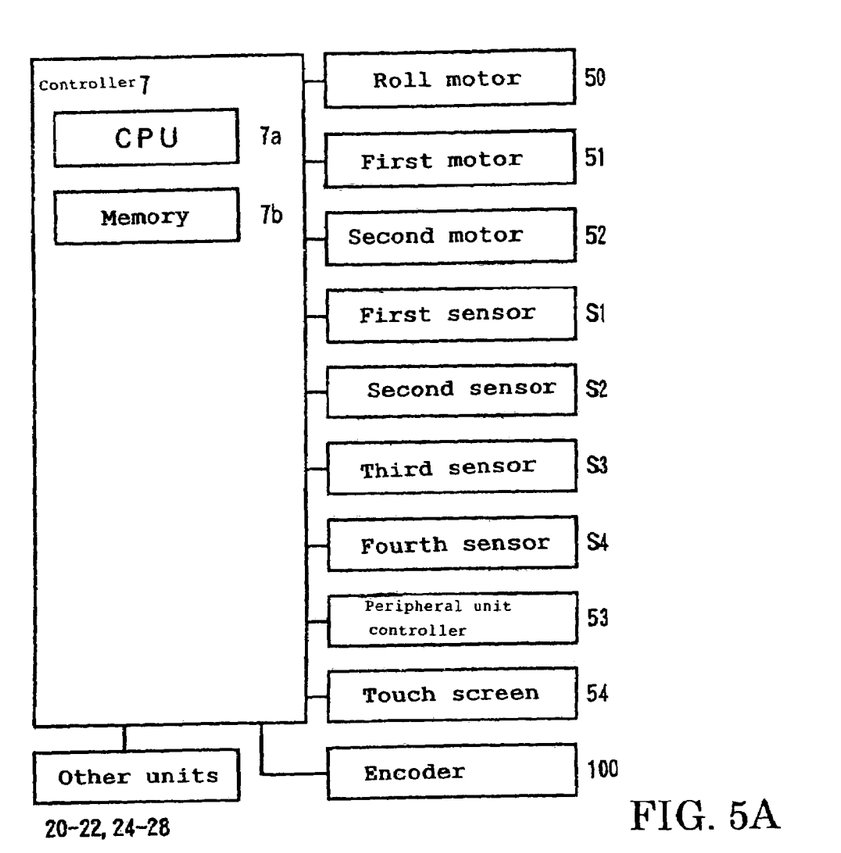
FIG. 5A is a schematic diagram illustrating a configuration of a placement device.
Figure 8:
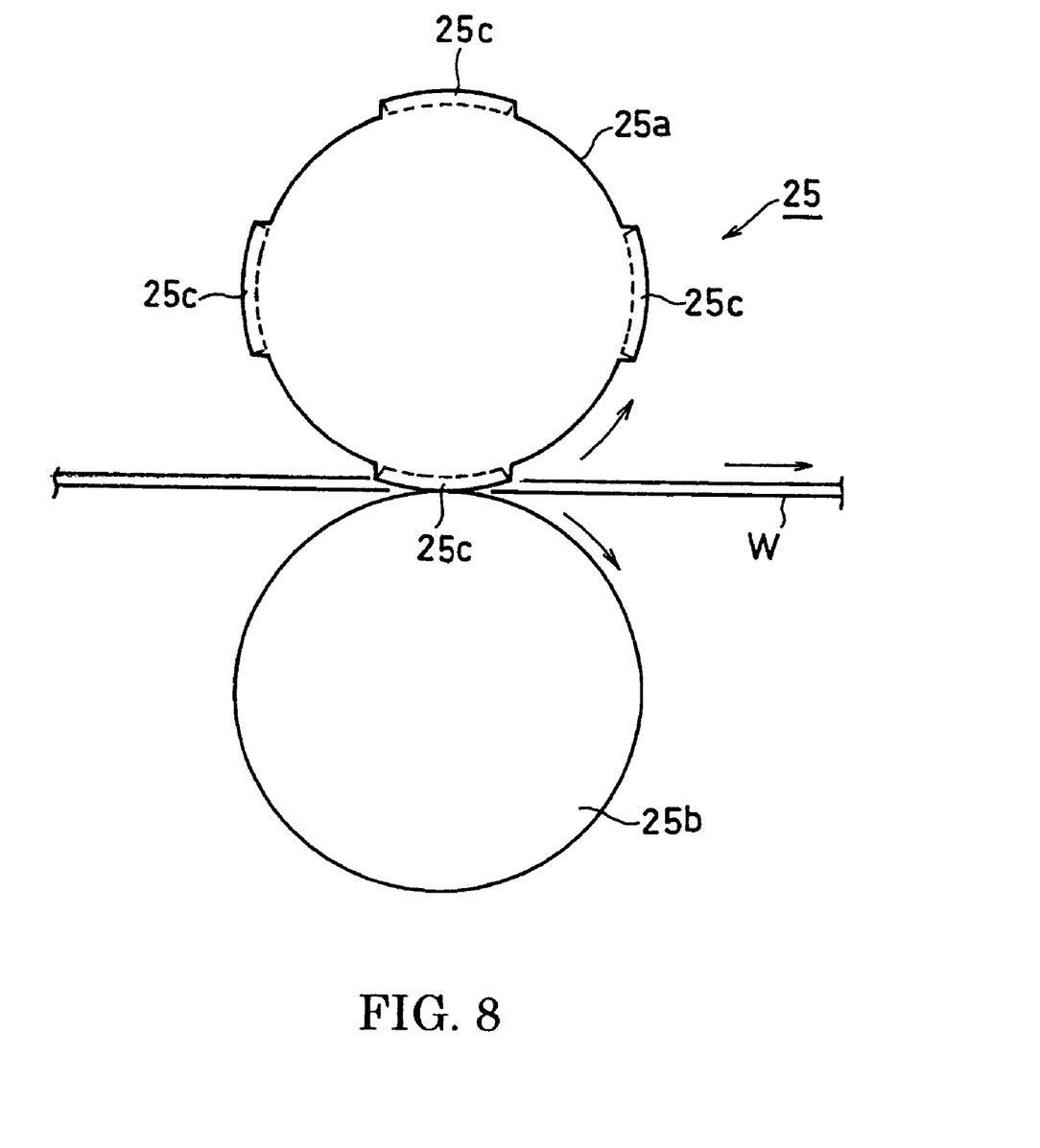
FIG. 8 is a schematic diagram illustrating a trim cutter unit.

In FIG. 1, the trim cutter unit 25 is provided downstream of the guide unit 23. As illustrated in FIG. 8, the trim cutter unit 25 includes a trim roll (die cutter) 25a including at least one loop-shaped blade 25c, and an anvil roll 25b, so that a portion located between the blade 25c and the anvil roll 25b is cut off. The phase of the trim roll 25a can be detected by an encoder 100 (FIG. 5A). The encoder 100 may be attached directly to the trim roll 25a, or to a transmission device for transmitting the power to the trim roll 25a. Note that the trim cutter unit 25 may alternatively be provided upstream of the guide unit 23. In such a case, holes are made in the webs W1 and W2 with different trim cutters (not shown), respectively.

Referring to FIG. 5A, the roll motor 50, the first motor 51, the second motor 52, first to fourth sensors S1 to S4 to be described later, and a peripheral unit control section 53 to be described later are connected to the controller 7 via an interface (not shown). The controller 7 controls these components. Other units such as the first seal unit 21, the second cutter unit 22, the assembly unit 24, the trim cutter unit 25, the folding unit 26, the second seal unit 27, the third cutter unit 28 and the encoder 100 may be connected to the controller 7. In such a case, the controller 7 can control the other units 21, 22, 24 to 28 based on information output from the encoder 100. The controller 7 controls the production of worn articles while synchronizing the other units 21, 22, 24 to 28 and the guide unit 23 with one another. Moreover, the other units 21, 22 and 24 to 28 may include a controller. In such a case, the controller 7 is adapted to exchange information with the other units 21, 22 and 24 to 28, such as sync information and phase information for the operation thereof.

Note that a touch screen 54 for allowing the user to input operation information, for example, may be connected to the controller 7. The touch screen 54 is capable of displaying various information thereon while sensing the user's touch to accept inputs from the user.

Figure 5B:
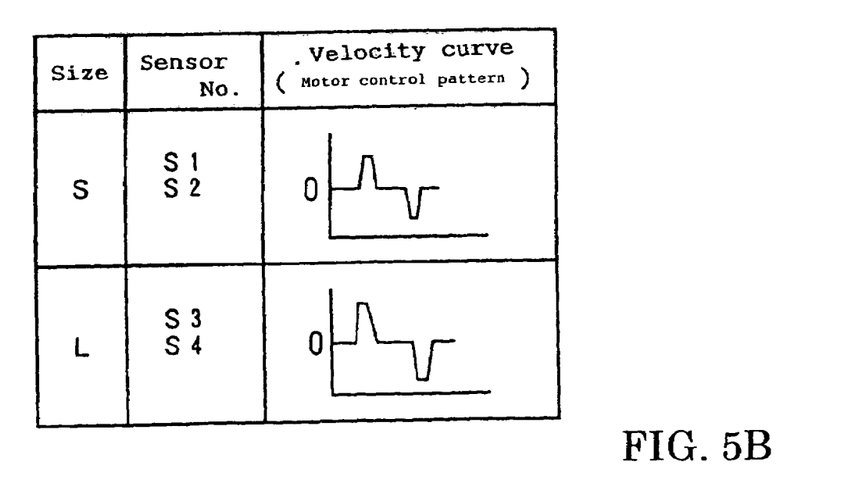
FIG. 5B is a table showing a set of information to be stored in a storage section.

The controller 7 includes a CPU 7a and a memory 7b. The CPU 7a is capable of executing a production process for producing articles or a positioning process for positioning the various units to their initial positions. The memory 7b includes a pattern storage section. Article sizes, sensor numbers, arrangement patterns of the elastic member Wf, and the velocity curves (motor control patterns) for the first and second motors 51 and 52, are prestored in the pattern storage section while being associated with one another. FIG. 5B shows an example of information stored in the pattern storage section. The motor control pattern may be velocity curve data corresponding to the rotational speed of the motors 51 and 52, or rotational acceleration sampling data.

The controller 7 controls the rotational speed, the rotational acceleration, etc., of the motors 51 and 52, based on the information read out from the pattern storage section. The control by the controller 7 may be feed-forward control, feedback control, fuzzy control, optimal control, neural control, robust control, or the like. In a case where feedback control is used, for example, the controller 7 reads out, from the memory 7b, rotation information of the motors 51 and 52 corresponding to the information on the arrangement of the elastic member Wf for the pattern being selected, and controls the voltages to be applied to the motors 51 and 52, the currents flowing through the motors 51 and 52, and/or the frequencies thereof, based on the readout data.

In a case where an elastic member is arranged periodically, the position information of the webs W1 and W2 may be fed back to the controller 7 in order to prevent the elastic member Wf and the webs W1 and W2 from being shifted from each other in the web flow direction. The position information of the webs W1 and W2 may be obtained by actually measuring the flow of the webs W1 and W2 with sensors (optical sensors, infrared sensors, ultrasonic sensors, air sensors, or the like), may be calculated from the rotation information of the nip rolls 1 and 2, or may be determined based on both the measurement values from the sensors and the rotation information so as to improve the precision. The rotation information of the nip rolls 1 and 2 is measured directly or indirectly via an encoder, etc., and sent to the controller 7.

The controller 7 produces a control signal for controlling the motors 51 and 52 based on the position information of the webs W1 and W2 and the velocity curves read out from the pattern storage section 7c. The motors 51 and 52 are controlled based on the control signal, and the rotational energies from the motors 51 and 52 are transmitted directly or indirectly to the guide sections 5a and 6a, respectively.

With such a control signal, when the motors 51 and 52 rotate in the forward direction (the clockwise direction in FIG. 3), whereby the pulleys 15a and 16a rotate in the forward direction, the arms 5 and 6 each move in the direction MD1 (hereinafter referred to as the "forward direction") from second positions 61 and 66 toward first positions 60 and 65 (the first positions 60 and 65 and the second positions 61 and 66 are the opposite ends of the moving range of the arms 5 and 6, respectively). On the other hand, when the pulleys 15a and 16a rotate in the reverse direction (the counterclockwise direction), the arms 5 and 6 each move in the direction MD2 (hereinafter referred to as the "reverse direction") from the first position 60 and 65 toward the second position 61 and 66.

The guide unit 23 operates in synchronization with a cutter unit such as the trim cutter unit 25 and/or a seal unit such as the first seal unit 21. In a case where the cutter unit and/or the seal unit have a mechanism such that they receive power from a main shaft, for example, the controller 7 synchronizes the operation of the guide unit 23 with other units that receive their power from the main shaft, based on the information from an encoder or encoders attached to the main shaft, the cutter unit and/or the seal unit. In a case where a servomotor, or the like, is used to drive the cutter unit and/or the seal unit, the controller 7 synchronizes the operation of the guide unit 23 with the other units, based on information from an encoder connected to the servomotor.

However, even if the units operate at the same cycle, the production apparatus cannot produce good products unless the units are controlled in phase with one another. In order to produce good products from immediately after the start-up of the production apparatus, it is necessary to control the guide unit 23 and the other units in phase with one another. A phase-matching method will now be described for the trim cutter unit 25, for example.

The inertia of the trim roll 25a of the trim cutter unit 25 is greater than that of the first and second arms 5 and 6 of the guide unit 23. Therefore, the operation of the first and second arms 5 and 6 is initiated from predetermined positions when the trim roll 25a comes to a predetermined position. Thus, the first and second arms 5 and 6 need to be placed in advance at the predetermined positions, e.g., original positions. Therefore, the guide unit 23 includes sensors S1 and S2 for indicating the original positions.

The controller 7 moves the arms 5 and 6 to the original positions upon receiving a return-to-origin signal. The controller 7 stops the rotation of the motors 51 and 52 when it is determined that the sensors S1 and S2 have detected the first and second arms 5 and 6. Thus, the first and second arms 5 and 6 can return to their original positions.

A sensing portion (e.g., a light-receiving portion) of each of the sensors S1 and S2 has a predetermined width Sa, and the controller 7 determines that the arms 5 and 6 are at their original positions when the sensing portion is shaded to a predetermined degree or more. Therefore, if the arms 5 and 6 approach the sensors S1 and S2 from different directions, there occurs an amount of error in the original position corresponding to the width Sa of the sensing portion (or the difference therebetween in the width of the dead zone, etc.).

In the present apparatus, the controller 7 considers signals from the sensor S1 as valid when the arm 5 moves in a predetermined direction, i.e., from one end of the moving range (e.g., the second position 61 toward the other end (e.g., the first position 60). On the other hand, when the arm 5 moves in a second direction opposite to the first direction, the controller 7 may consider signal from the sensor S1 as invalid. Therefore, the position of the arm 5 can be determined accurately, irrespective of the width of sensing area of the sensor S1, the direction dependence hysteresis of the sensor S1, and the insensitivity of sensing area of the sensor.

A similar process is performed for the arm 6 and the second sensor S2. When the arms 5 and 6 move in the first direction, the signals from the sensors S1 and S2 may be invalid. When the arm 5 moves in the first direction and the arm 6 moves in the second direction, the signals from the sensors S1 and S2 may be invalid. When the arm 5 moves in the second direction and the arm 6 moves in the first direction, the signals from the sensors S1 and S2 may be invalid. When the arms 5 and 6 move in the second direction, the signals from the sensors S1 and S2 may be invalid. Note that the controller 7 controls the first and second motors 51 and 52, and thus knows, beforehand, the direction in which the arms 5 and 6 are going to move. Moreover, as long as the sensors S1 and S2 can detect the arms 5 and 6, the guide sections 5a and 6a, etc., the sensors S1 and S2 may be of any type. For example, the sensors S1 and S2 may be optical sensors, infrared sensors, ultrasonic sensors, air sensors, or the like. Their sensors have a least one of a width of sensing area, a direction dependence hysteresis, and insensitivity of sensing area.

Figure 6:
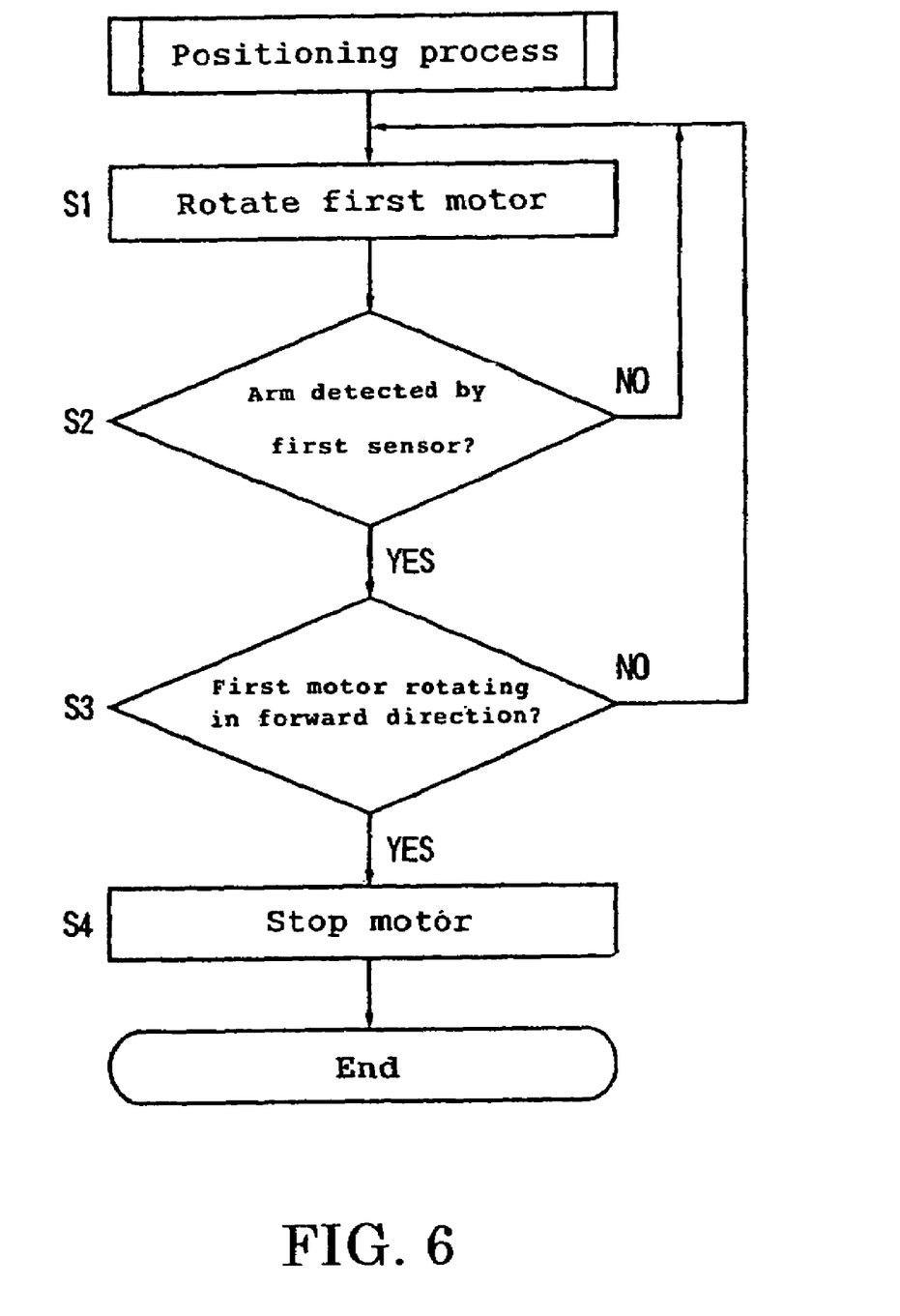
FIG. 6 is a flow chart illustrating a positioning process.

An example of a positioning process will be described with reference to the flow chart of FIG. 6.

Upon receiving a return-to-origin signal, the controller 7 rotates the motor 51 (step S1). When the arm 5 reaches an end (e.g., the first position 60 or the second position 61), the arm 5 turns back. Upon making the turn, the first motor 51 starts rotating in the opposite direction. When the controller 7 detects the first arm 5 based on a signal from the first sensor S1, the process proceeds to step S3. Otherwise, the process proceeds to step S1. In step S3, the controller 7 determines whether the arm 5 is moving in the first direction or in the second direction opposite to the first direction. For example, the controller 7 determines the moving direction to be the first direction if the first motor 51 is rotating in the forward direction, and determines the moving direction to be the second direction if the first motor 51 is rotating in the reverse direction. Alternatively, a sensor (not shown) for directly measuring the moving direction of the arm 5 may be attached to the guide unit 23. When the arm 5 is moving in the first direction, the process proceeds to step S4, where the controller 7 stops the rotation of the motor 51. When the arm 5 is moving in the second direction, the process proceeds to step S1, and the positioning process continues. Note that a similar process is performed for the second sensor S2.

After completion of the process of positioning the arms 5 and 6, the trim cutter unit 25, etc., are rotated, and the arms 5 and 6 are activated when the trim cutter unit 25, etc., come to a predetermined position, whereby the guide unit 23 and the other units can be controlled in phase with one another. For example, controller 7 can activate the motors 51 and 52 upon learning that the trim cutter unit 25, etc., have reached the predetermined position based on information from an encoder connected to the trim cutter unit 25, etc. Note that controller 7 may activate the motors 51 and 52 slightly before the predetermined position is reached (by a predetermined amount of time), taking into consideration the time lag from when the predetermined position is reached until the motors 51 and 52 start moving.

When producing an article of a different size, the original positions of the arms 5 and 6 are normally different from those indicated by the first and second sensors S1 and S2. Therefore, the guide unit 23 may include additional sensors for indicating original positions for articles of different sizes. In the guide unit 23, different combinations of sensors each corresponding to a different size of an article to be produced, the target velocity curves for one cycle of the motors, etc., are stored in the memory 7b, and the CPU 7a is capable of reading out and processing such information. FIG. 5B shows an example of a set of information stored in the memory 7b, including article sizes, sensor combinations and target velocity curves (where the vertical axis represents the target velocity of the motor, and the horizontal axis represents the cycle).

For example, when producing an article of a size different from the size of the article being currently produced, the operator performs a predetermined operation to stop the operation of the present apparatus. Then, the operator specifies the article to be produced next by using the touch screen 54, in response to which the CPU 7a reads out, from the memory 7b, sensor numbers and motor velocity curves corresponding to the size of the article to be produced next. When an article of size L is to be produced, third and fourth sensors S3 and S4 are selected. As with the sensors S1 and S2, the controller 7 stops the arms 5 and 6 at their original positions based on signals from the third and fourth sensors S3 and S4 and the moving direction of the arms 5 and 6.

Some methods for producing the combined web W by using the guide unit 23 as described above will now be described.

First method: An adhesive for bonding the elastic member Wf is applied continuously or intermittently on at least one of the two webs W1 and W2. The webs W1 and W2 are passed to the nip rolls 1and 2. As the guide sections 5a and 6a move in the direction MD across the first web W1, the elastic member Wf to be sandwiched between the webs W1 and W2 can be placed in a predetermined pattern. The controller 7 controls the motors 51 and 52 based on the motor control pattern read out from the memory 7b. The elastic member Wf is guided between the two webs W1 and W2, and the elastic member Wf and the webs W1 and W2 are pressed together by the nip rolls 1and 2 into a single member. Note that in a case where the adhesive is applied intermittently, there are portions where the elastic member Wf is not bonded onto the webs W1 and W2. Such portions of the elastic member Wf may be cut off in a subsequent step.

Second method: The elastic member Wf having a heat-sealable member is guided between the two webs W1 and W2. The elastic member Wf is heated by the nip rolls 1 and 2 while the two webs W1 and W2 are nipped by the nip rolls 1 and 2, thereby bonding the elastic member Wf and the webs W1 and W2 together. Note that an adhesive may be applied to portions where the webs W1 and W2 need to be connected together.

Figure 9:
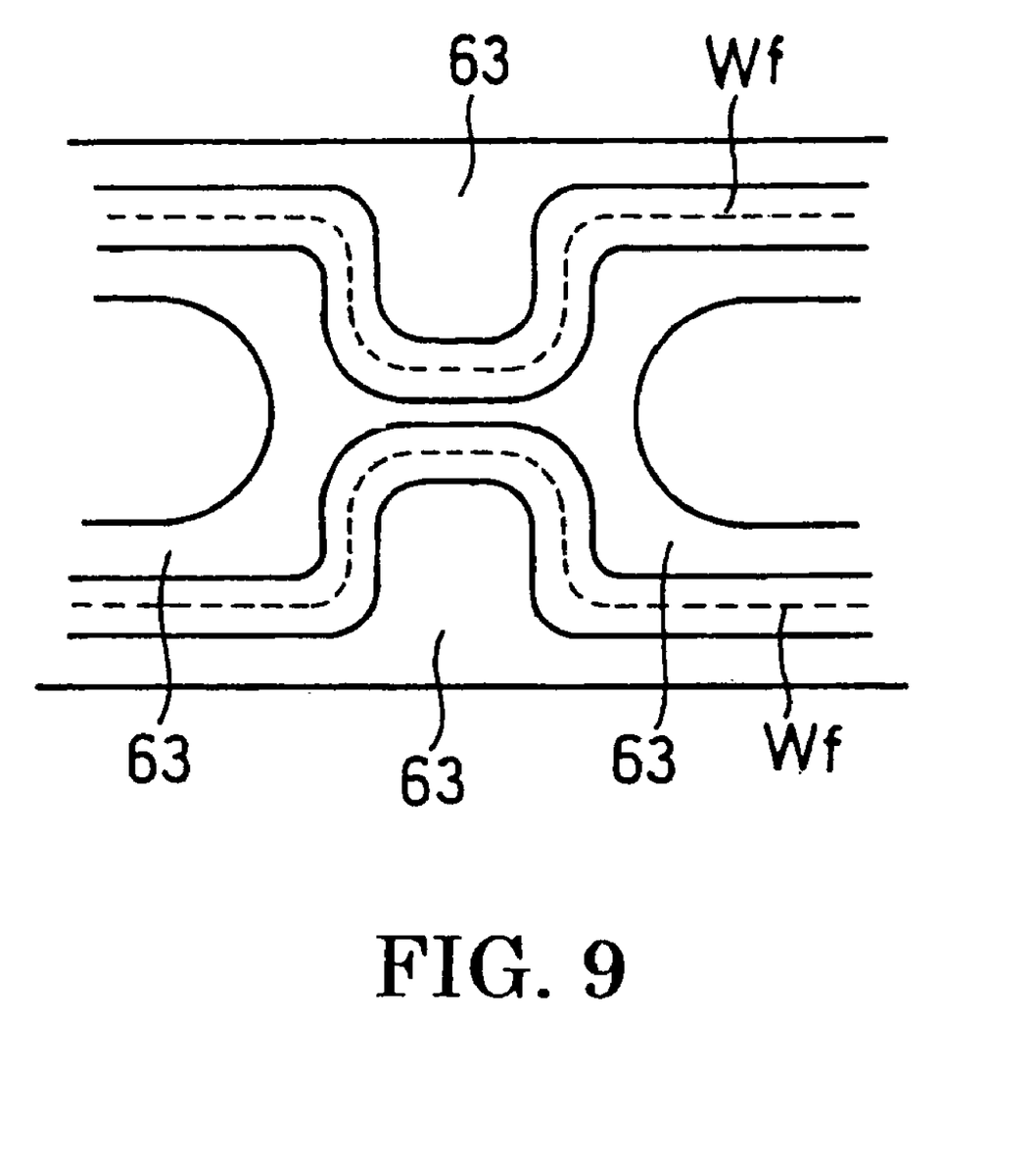
FIG. 9 is a diagram illustrating an example of a combined web.

Third method: An adhesive for bonding together the webs W1 and W2 is applied continuously or intermittently on at least one of the two webs W1 and W2. The elastic member Wf is guided between the two webs W1 and W2, and pressed together by the nip rolls 1 and 2 into a single member. Note however that elastic member Wf is not bonded to the webs W1 and W2 by the adhesive. In other words, an area 63 with an adhesive applied thereon is formed so as to surround the elastic member Wf, thereby restricting the position of the elastic member Wf, as illustrated in FIG. 9. As compared to articles produced by the first or second method, the air permeability at positions where the elastic member Wf is placed is higher in articles produced by the third method. Portions where the elastic member Wf is placed will be in contact with the wearer, and if the elastic member Wf is fixed directly by an adhesive, the air permeability is lowered by the adhesive.

Fourth method: The elastic member Wf is guided between the two webs W1 and W2. The webs W1 and W2 are nipped and also heat-embossed by the nip rolls 1 and 2. For example, the nip roll 1 (2) has a plurality of pin-like portions, and the nip roll 2 (1) functions as an anvil roll. The webs W1 and W2 are heat-bonded with each other at a plurality of positions by the plurality of pin-like portions being heated, whereby the position of the elastic member Wf is restricted by the heat-bonded portions.

Figure 10A:
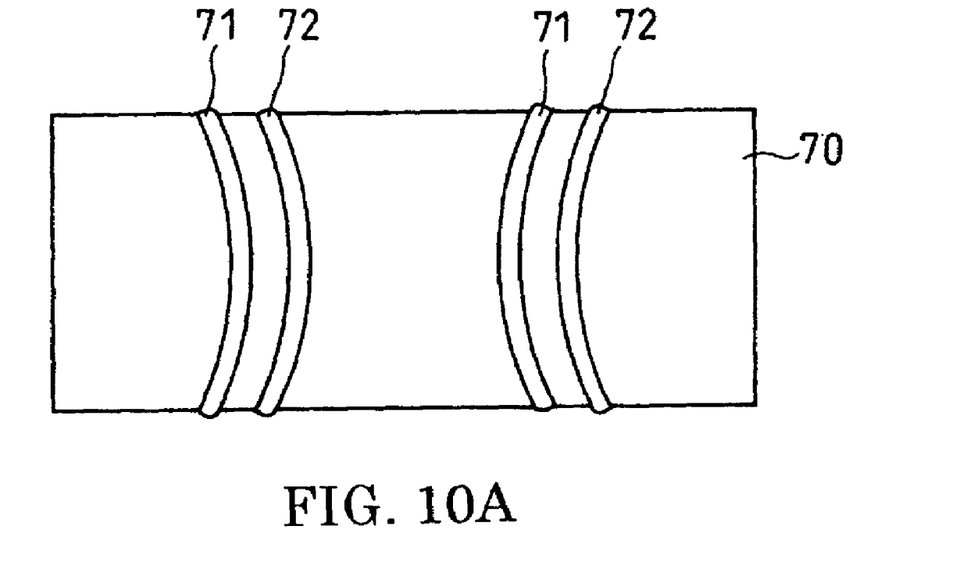
FIG. 10A is a diagram illustrating an example of an anvil 70.
Figure 10B:
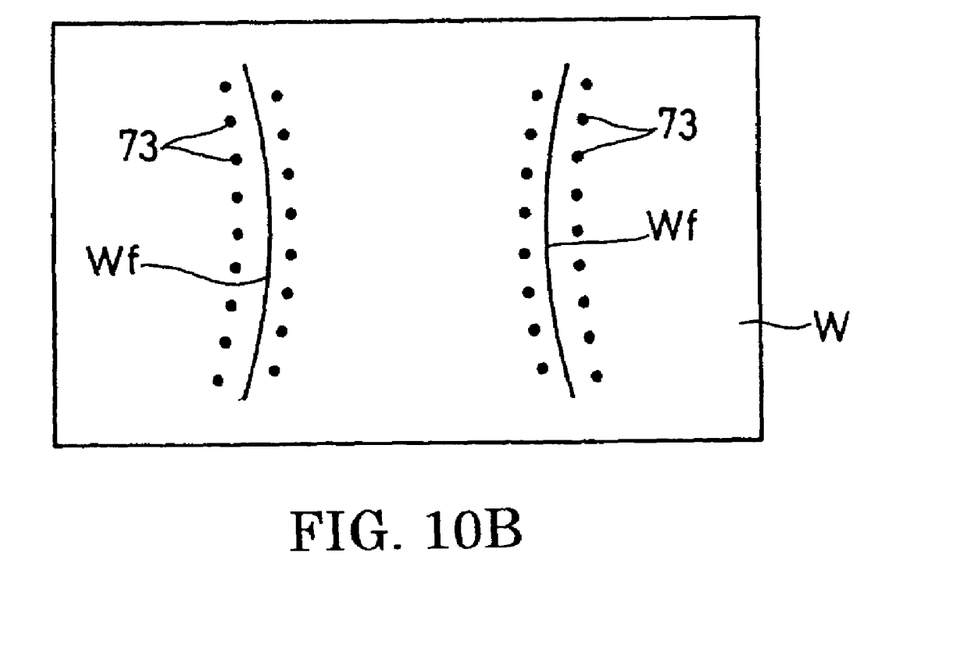
FIG. 10B is a diagram illustrating an example of a combined web.

Fifth method: The elastic member Wf is guided between the two webs W1 and W2. The webs W1 and W2 are nipped by the nip rolls 1 and 2, and then the webs W1 and W2 are bonded together ultrasonically, whereby the position of the elastic member Wf is restricted by the bonded portions. FIG. 10A illustrates an anvil 70. The anvil 70 has patterns 71 and 72 shaped so as to interpose the elastic member Wf therebetween. Note that the patterns 71 and 72 do not need to be continuous, but may alternatively be a plurality of pin-like portions surrounding the elastic member Wf. FIG. 10B shows an example of a combined web that has been bonded by an anvil having a plurality of pin-like portions. The position of the elastic member Wf is restricted by bonded portions 73.

Figure 7A:
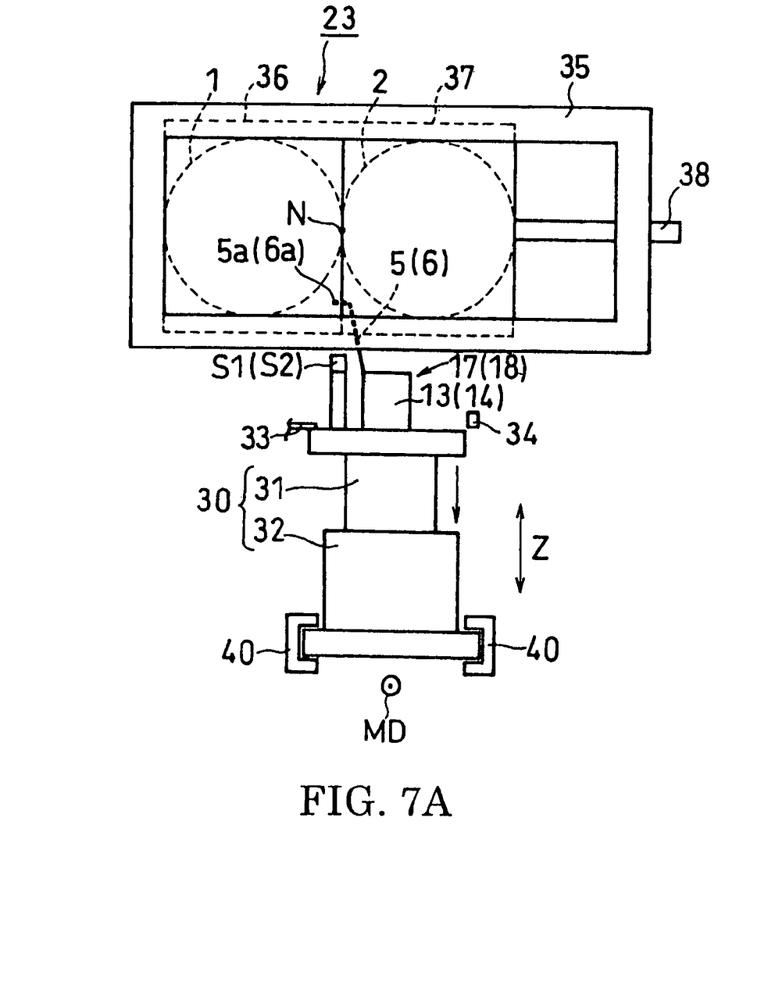
FIG. 7A and FIG. 7B are schematic side views illustrating a method for maintaining a placement device.
Figure 7B:
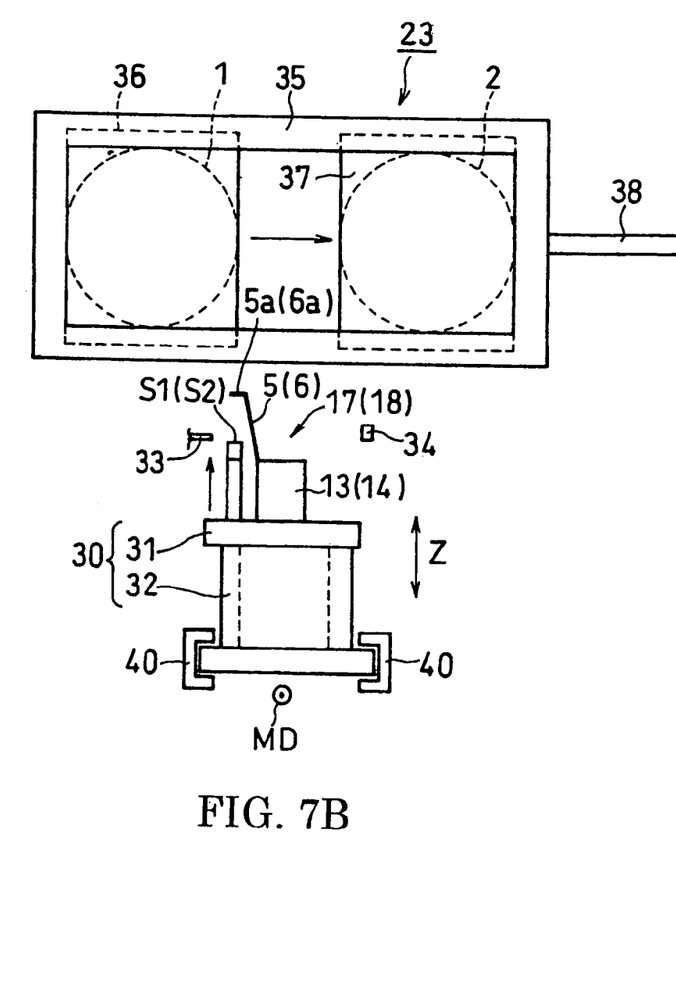

In the embodiment illustrated in FIG. 7A, the nip rolls 1 and 2 are housed in housings 36 and 37, respectively. At least one of the housings 36 and 37 is movable along a groove or a rail provided on a frame 35. The housing can be moved by rotating a screw 38. The moving device may be an air cylinder, or the like. When maintaining the production apparatus, the nip rolls 1 and 2 can be spaced apart from each other by moving the housing 37, as illustrated in FIG. 7B. The housings 36 and 37 may be held by an elastic member such as a spring.

The guide unit 23 includes a stand 30. The moving member 17 (18) including the transfer section 13 (14), the arm 5 (6), etc., is attached to the stand 30. The stand 30 includes a lift section 31 and a fixed section 32. The moving member 17 (18) is placed on the lift section 31. The lift section 31 can be moved in the first direction Z with respect to the fixed section 32 by an elevating device (not shown), for example. The first direction Z is the direction in which the moving member 17 (18), etc., are moved toward and away from the nip rolls 1 and 2. The elevating device may be an air cylinder, a motor, or the like. In a case where a motor is used, the elevating mechanism may employ cams, links, or screws.

In a case where the elevating mechanism uses an air cylinder, the present apparatus may include a stopper 33, whereby the lift section 31 is stopped from moving up over a predetermined distance in the first direction.

A sensor 34 may alternatively be provided instead of the stopper 33. The sensor 34 may be, for example, an optical sensor provided near the upper or lower end of the moving range of the lift section 31. When the sensor 34 detects the lift section 31, the lift section 31 is stopped. A similar stop device may be used also in a case where the elevating mechanism is a motor.

By moving the lift section 31, it is possible to change the distance between the nip point N between the nip rolls 1 and 2 and the guide sections 5a and 6a.

Moreover, the lift section 31 or the stand 30 may be movable in the axial direction of the nip rolls 1 and 2. For example, the present apparatus or the guide unit 23 may include a rail 40 extending in the width direction MD so that the stand 30, etc., can be moved in the width direction MD while being guided by the rail 40. Therefore, when the elastic member Wf is broken, for example, the stand 30 can be pulled out, whereby it is easy to pass the elastic member Wf through the holes of the guide sections 5a and 6a, after which the stand 30 can be moved back to the original position. Even when the stand 30, etc., cannot be pulled out due to the first or second arm 5 or 6 interfering with the frame 35, the arm 5 or 6 can be moved away from the frame 35 by using the lift section 31 of the stand 30.

Next, a maintenance method will be described.

When an adhesive is attached to the surface of the nip rolls 1 and 2 or the guide sections 5a and 6a, one of the nip rolls 1 and 2 being in the position of FIG. 7A is moved along a groove, etc., on the frame 35 so that the nip rolls 1 and 2 are spaced apart from each other, as illustrated in FIG. 7B. Then, the nip rolls 1 and 2, etc., can easily be cleaned. Moreover, an elastic member can easily be passed through the guide sections. The stand can be moved so as to move the guide sections 5a and 6a away from the nip rolls 1 and 2 to further facilitate the operation as described above. This further increases the operation efficiency.

Then, the stand 30 is pulled out from under the frame 35 along the rail 40.

Thus, the nip rolls 1 and 2 are spaced apart from each other, and the guide sections 5a and 6a can be moved to a more spacious place for easy maintenance.

Note that the elastic member Wf is sandwiched between the two webs W1 and W2 by the nip rolls 1 and 2 in the embodiment described above. Alternatively, the elastic member Wf may be placed onto a single web W1. The elastic member Wf may be fixed to the web W1 by applying an adhesive on the web W1 or by heat seal. In such a case, a material having a good peelability with respect to the adhesive, such as a silicone rubber, may be used for the nip rolls 1 and 2, or the nip rolls 1 and 2 may be cooled.

Leg holes, through which legs of the wearer are passed, may be made before the elastic member Wf is sandwiched by the two webs W1 and W2. An absorbent is placed on the webs W1 and W2 and the elastic member Wf, which have been nipped into a single laminate. The absorbent may be placed on the laminate before making the holes. The absorbent may include a highly absorbent polymer containing at least one of a pulp, an acrylic ester, and a water-soluble polysaccharide. Moreover, the absorbent may include an airlaid material. The laminate, on which the absorbent has been placed, is cut off into pieces of a predetermined length (pitch) by using a cutter. The cut-off web piece is folded as necessary. Note that before the laminate is cut off by a cutter, the continuous laminate may be folded in two along the web flow direction.

Curved fit gathers as shown in Japanese Laid-Open Patent Publication No. 7-299094 may be formed along with the leg gathers. Note that in order to place curved fit gathers on diapers with no leg gathers, a pattern for placing fit gathers may be used instead of a pattern for forming the leg gathers.

As described above, with the device for placing an elastic member of the present invention, the original position is set based on a detection signal from the sensor when the moving member approaches the sensor while moving in the first direction. Therefore, it is possible to accurately detect the position of the moving member even if the sensing section of the sensor has a width, a direction dependence hysteresis, insensitivity of sensing area, or the like. Therefore, it is possible to accurately form a line of the elastic member by determining the original position of the moving member based on such detection.

Moreover, for different sizes of worn articles, a plurality of sensors are provided, and different motor control patterns are stored in a memory device, whereby the elastic member can be placed with a different original position and a different arrangement pattern for each size.

Moreover, the nip rolls are provided so that at least one nip roll can be moved away from the other nip roll, so that the nip rolls can be spaced apart from each other when maintaining the production apparatus, thereby improving the maintainability.

Moreover, the stand can be moved so that the guide section is moved away from the nip point between the pair of nip rolls, thereby further improving the maintainability.

Moreover, the moving member and the transfer section can be moved along the axial direction of the nip rolls, whereby the guide section can be pulled out from under the nip rolls, thus further improving the maintainability.

What is claimed is:

1. A placement device, comprising:
   a guide section for guiding an elastic member;
   a first nip roll and a second nip roll for pressing together the elastic member and a web;
   a transfer section capable of transferring the guide section across the web; and
   an indicating section for indicating a position,
   wherein when the guide section comes close to the position while moving in a first direction, the transfer section can stop transferring the guide section in response to a signal from the indicating section.

2. A placement device according to claim 1, wherein:
   the transfer section includes a motor capable of rotating in a first rotation direction and a second rotation direction opposite to the first rotation direction, whereby a moving direction of the guide section can be changed by changing a rotation direction of the motor;
   the indicating section is a sensor for detecting the guide section or the transfer section, and is capable of indicating that the guide section is located at the position; and
   if the sensor detects the guide section or the transfer section when the rotation direction of the motor is the first direction, a controller can stop the rotation of the motor.

3. A placement device according to claim 1, wherein:
   a plurality of the sensors are arranged along a transfer direction of the transfer section;
   the plurality of sensors indicate a plurality of positions necessary for producing products of different sizes;
   the controller selects at least one of the sensors associated with a size of a product to be produced; and
   the controller controls the motor according to the size of the product to be produced.

4. A placement device according to claim 1, wherein at least one of the first and second nip rolls can be moved.

5. A placement device according to claim 1, further comprising a stand on which the transfer section is placed, wherein the stand is movable so that a distance between a nip point between the nip rolls and the guide section can be changed.

6. A placement device according to claim 1, wherein the stand is movable along an axial direction of the nip rolls.

7. A placement device according to claim 1, wherein the elastic member is sandwiched between the web and another web.

8. A placement device according to claim 1, wherein an adhesive for fixing the elastic member is applied continuously or intermittently on the web.

9. A placement device according to claim 7, wherein an adhesive is applied continuously or intermittently on the web so as to surround the elastic member when the elastic member is placed on the web.

10. A placement device according to claim 1, wherein the elastic member includes a heat-sealable member, and the elastic member and the web are heat-sealed together by the first and second nip rolls.

11. A placement device according to claim 7, wherein the first nip roll includes a plurality of protrusions while the second nip roll functions as an anvil so that the protrusions melt portions of the web and another web to bond the webs to each other at a plurality of bonding points, whereby a position of the elastic member is restricted by the plurality of bonding points.

12. A method for producing a worn article, wherein the guide section is placed at the position by using a placement device according to claim 1, after which a cutter drum including a blade is rotated, and the transfer section starts transferring the guide section when the blade is rotated to reach a predetermined position.

* * * * *